(12) United States Patent
Sookram et al.

(10) Patent No.: US 10,463,042 B2
(45) Date of Patent: *Nov. 5, 2019

(54) ANTI-MICROBIAL COMPOSITIONS AND RELATED METHODS

(71) Applicant: NBIP, LLC, Plano, TX (US)

(72) Inventors: Burt R. Sookram, Palm Harbor, FL (US); John W. Veenstra, Plano, TX (US)

(73) Assignee: NBIP, LLC, Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/356,595

(22) PCT Filed: Nov. 6, 2012

(86) PCT No.: PCT/US2012/063670
§ 371 (c)(1),
(2) Date: May 6, 2014

(87) PCT Pub. No.: WO2013/067544
PCT Pub. Date: May 10, 2013

(65) Prior Publication Data
US 2014/0308265 A1  Oct. 16, 2014

Related U.S. Application Data

(60) Provisional application No. 61/556,264, filed on Nov. 6, 2011, provisional application No. 61/556,241, filed on Nov. 6, 2011, provisional application No. 61/556,247, filed on Nov. 6, 2011.

(51) Int. Cl.
*A01N 25/02* (2006.01)
*A01N 37/04* (2006.01)
*A01N 43/40* (2006.01)

(52) U.S. Cl.
CPC ............. *A01N 37/04* (2013.01); *A01N 25/02* (2013.01); *A01N 43/40* (2013.01)

(58) Field of Classification Search
None
See application file for complete search history.

(56) References Cited

U.S. PATENT DOCUMENTS

| | | | |
|---|---|---|---|
| 4,764,365 A | 8/1988 | Boothe et al. | |
| 5,753,614 A | 5/1998 | Blackburn et al. | |
| 7,824,524 B2 * | 11/2010 | Sakovich et al. | 204/157.49 |
| 2007/0027119 A1 * | 2/2007 | Ahmed | A01N 31/02 |
| | | | 514/159 |
| 2007/0048344 A1 | 3/2007 | Yahiaoui et al. | |
| 2007/0082018 A1 * | 4/2007 | Weiss | A23L 3/3463 |
| | | | 424/400 |
| 2008/0145390 A1 * | 6/2008 | Taylor et al. | 424/405 |
| 2010/0006418 A1 | 1/2010 | Sakovich et al. | |
| 2010/0273885 A1 | 10/2010 | Davis | |
| 2010/0298386 A1 | 11/2010 | Burwell | |
| 2011/0207786 A1 | 8/2011 | Callahan et al. | |

FOREIGN PATENT DOCUMENTS

| WO | WO-0167878 A1 | 9/2001 |
|---|---|---|
| WO | WO2009045456 * | 4/2009 |

OTHER PUBLICATIONS

ChemIDplus, Oxalic Acid, http://chem.sis.nlm.nih.gov/chemidplus/rn/144-62-7, retrieved online on Feb. 3, 2016.*
Merriam-Webster's Learner's Dictionary, Definition of Proton, retrieved online on Dec. 8, 2016.*
The Pharmaceutics and Compounding Laboratory, Commonly Used Emulsifiers and Their HLB Values, http://pharmlabs.unc.edu/labs/emulsions/hlb.htm, retrieved online on Mar. 14, 2017.*

* cited by examiner

*Primary Examiner* — Jennifer A Berrios
(74) *Attorney, Agent, or Firm* — Winstead PC

(57) ABSTRACT

The claimed invention is directed to compositions and methods effective in preventing microbial contamination or reducing microbial count associated with a contaminated surface, comprising a biocidal system comprised of a primary biocide, a pH buffer agent, a surfactant, all in an aqueous based carrier, wherein the compositions may be considered environmentally friendly.

5 Claims, No Drawings

ANTI-MICROBIAL COMPOSITIONS AND RELATED METHODS

CROSS-REFERENCES TO RELATED APPLICATIONS

This Application claims the benefit under 35 U.S.C. § 119(e) of U.S. Provisional Patent Application Ser. No. 61/556,264, filed Nov. 6, 2011, U.S. Provisional Patent Application Ser. No. 61/556,241, filed Nov. 6, 2011, and U.S. Provisional Patent Application Ser. No. 61/556,247, filed Nov. 6, 2011, all of which are incorporated herein by reference in their entirety as if fully set forth herein.

FIELD OF THE INVENTION

The present disclosure relates to compositions and methods that are effective in preventing microbial contamination or reducing the microbial count on or in a contaminated surface.

BACKGROUND OF THE INVENTION

Mold, mildew, fungi, viral and bacterial (microbial) contamination is undesirable on many types of surfaces. Control of such microbial contamination has largely been based on the use of biocides that have limited efficacy and may have a harmful effect on the environment. Therefore, the use of more effective biocides or derivatives thereof that may be more effective in microbial control is desirable. An additional benefit may be that compositions may be environmentally friendly which is also desirable in certain applications.

The anti-microbial properties of quaternary ammonium compounds are generally known. Such compounds have been used extensively in cleaning compositions for domestic and industrial applications. However, it would be preferable to use smaller amounts of these compounds in cleaning compositions since they can be harmful to the environment and minimally effective. Therefore, it would be desirable to create formulations comprising compounds that exhibit anti-microbial properties and may at the same time be environmental friendly.

SUMMARY OF THE INVENTION

The claimed invention relates to compositions and methods that are effective in preventing microbial contamination or reducing the microbial count on or in a contaminated surface.

The disclosed compositions comprise a biocidal system comprising a primary biocide, a pH buffer, and a surfactant in an aqueous based carrier.

An embodiment of the invention is directed to a composition the composition comprising:
a. from about 0.01% to about 20.0% by weight of a biocidal system comprising:
   i. from about 0.01% to about 25% by weight of a primary biocide; and
   ii. at least about 0.01% to about 25% by weight of a pH buffer, where the pH buffer is a biocidal, dermal, non-corrosive acid composition, having a proton count range of from $1.0 \times 10^{20}$ to $9.9 \times 10^{26}$, an embodied conductivity range of from 250 mV to 1500 mV and has a pH of less than 2.0 when the pH buffer is present at a concentration of 0.1% by weight; and
b. from about 0.01% to 4.0% by weight of a surfactant; and
c. the balance being an aqueous based carrier.

DETAILED DESCRIPTION OF EXEMPLARY EMBODIMENTS

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a carrier" includes mixtures of two or more such carriers, and the like.

Ranges may be expressed herein as from "about" one particular value, and/or to "about" another particular value. When such a range is expressed, another aspect includes from the one particular value and/or to the other particular value. Similarly, when values are expressed as approximations by use of the antecedent "about," it will be understood that the particular value forms another aspect. It will be further understood that the endpoints of each of the ranges are significant both in relation to the other endpoint and independently of the other endpoint.

"Admixture" or "blend" as generally used herein means a physical combination of two or more different components By "contacting" is meant an instance of applying a composition to a contaminated surface.

"Contamination" is used herein to describe microbiological intrusions, such as the presence of toxins or pathogens in or on the surface of any material.

"Controlled release" as used herein means the use of a material to regulate the release of another substance.

"Effective amount" as used herein means an amount of a composition as disclosed herein, effective at dosages and for periods necessary to achieve the desired result.

"Environmentally friendly" as used herein refers to green, organic or natural compositions that are minimally harmful to the environment.

"Excipient" is used herein to include any other compound that may be contained in or on the microparticle that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

"Microbiological" as used herein refers to any inclusion or growth of harmful microorganisms such as mold, mildew, viral or bacterial contamination.

"Microbial Count" as used herein refers to the amount or number of microbiological contaminates present on any surface.

"Optional" or "optionally" means that the subsequently described event or circumstance can or cannot occur, and that the description includes instances where the event or circumstance occurs and instances where it does not.

"Primary biocide" is used herein to refer to compositions that are biologically active against microbial contaminates.

"Primary pathogen" is used herein to refer to mold, mildew, bacteria, viruses or other microorganisms that can cause contamination on a surface.

By "sufficient amount" and "sufficient time" means, an amount and time needed to achieve the desired result or results, e.g., control and/or prevention of microbial contamination.

"Surface" as used herein refers to the object that contains the microbiological contamination. The term surface can apply to the entire object, a portion or layer of the object, and down to the molecular structure of the object.

A "weight percent" of a component, unless specifically stated to the contrary, is based on the total weight of the formulation or composition in which the component is included.

The present disclosure addresses solutions to several unmet needs as defined below:
1. Providing compositions effective in killing one or more bacterial pathogens. Non-limiting examples include *Salmonella, Pseudomonas aeruginosa, Staphylococcus aureus, Staphylococcus epidermdis, Streptococcus agalactiae, Pseudomonas* species. *Campylobacter jejuni, Escherichia coli, (E. coli)* and *Klebsiella pneumonia*.
2. Providing compositions effective in killing one or more viral pathogens. Non-limiting examples which includes *Cryptosporidium, Giardia lamblia*, poliomyelitis, meningitis, and gastroenteritis, Rotaviruses, Norwalk, Norovirus, Hepatitis A, parasites.
3. Providing compositions effective in killing one or more mold and mildew spores pathogens. Non-limiting examples which includes *Trichophyton mentagrophytes, Guignardia citricarpa*, and *Colletotrichum acutatum*.
4. Providing compositions that are a replacement for chlorine and chlorine based products such as sodium hypochlorite based treatments.

Treatment Compositions

The inventive composition generally includes a biocide system, which includes a primary biocide and a pH buffering component. The primary biocide is selected according to the nature of the microorganisms sought to be controlled, for example, a quaternary ammonium salt. The pH buffer is mechanically fused so as to aid in the delivery of the primary biocide without causing damage to the surface being treated. By way of example, a suitable pH buffer is disclosed in U.S. Pat. No. 7,824,524, which is incorporated by reference herein in its entirety, or in a U.S. patent application Ser. No. 13/346,160, entitled "Reactive, non-corrosive and dermal-friendly composition and methods for manufacturing" which is also incorporated by reference herein in its entirety. In embodiments of the invention, the pH buffer is chosen for compatibility with the primary biocide.

An embodiment of the invention relates to compositions that are effective in preventing or reducing microbial count, the composition comprising:
  a. from about 0.01% to about 20.0% by weight of a biocidal system comprising:
    i. from about 0.01% to about 25% by weight of a primary biocide; and
    ii. at least about 0.01% to about 25% by weight of a pH buffer, where the pH buffer is a biocidal, dermal, non-corrosive acid composition, having a proton count range of from $1.0 \times 10^{20}$ to $9.9 \times 10^{26}$, an embodied conductivity range of from 250 mV to 1500 mV and has a pH of less than 2.0 when the pH buffer is present at a concentration of 0.1% by weight; and
  b. from about 0.01% to 4.0% by weight of a surfactant; and
  c. the balance being an aqueous based carrier.

However, other non-limiting embodiments and combinations are possible as further disclosed herein.

Biocidal System

The disclosed compositions comprise a biocidal system. The biocidal system comprises a primary biocide and a pH buffer. In certain embodiments of the invention, the disclosed compositions comprise from about 0.01% to about 20.00% by weight of a biocidal system. In other embodiments, the biocidal system comprises at least about 25% by weight of a primary biocide and at least about 25% by weight of a pH buffer component. The pH buffer is chosen for compatibility with the primary biocide.

Primary Biocide

A first group of suitable biocides include quaternary ammonium compounds chosen from ($C_{12}$-$C_{14}$ alkyl)($C_1$-$C_2$ dialkyl)benzyl ammonium salts, N—($C_{12}$-$C_{18}$ alkyl)heteroaryl ammonium salts, and N—[($C_{12}$-$C_{14}$ alkyl)($C_1$-$C_2$ dialkyl)]heteroarylalkylene ammonium salts. Non-limiting examples of the ($C_{12}$-$C_{14}$ alkyl)($C_1$-$C_2$ dialkyl)benzyl ammonium salts include ($C_{12}$-$C_{14}$ alkyl)dimethyl-benzyl ammonium chloride, ($C_{12}$-$C_{14}$ alkyl)dimethylbenzyl ammonium bromide, and ($C_{12}$-$C_{14}$ alkyl)dimethylbenzyl ammonium hydrogen sulfate. Non-limiting examples of the N—($C_{12}$-$C_{18}$ alkyl)heteroaryl ammonium salts include cetyl pyridinium chloride, cetyl pyridinium bromide, and cetyl pyridinium hydrogen sulfide. For the N—($C_{12}$-$C_{18}$ alkyl) heteroaryl ammonium salts other anions can be used.

Further examples of quaternary ammonium compounds suitable for use as the primary biocides include cetyltrimethylammonium chloride, stearyltrimethylammonium chloride, isostearyltrimethylammonium chloride, lauryltrimethylammonium chloride, behenyltrimethyl-ammonium chloride, octadecyltrimethylammonium chloride, cocoyltriinethylammonium chloride, cetyltrimethylammonium bromide, stearyltrimethylammonium bromide, lauryl-trimethylammonium bromide, isostearyllauryldimethylammonium chloride, dicetyldimethylammonium chloride, distearyldimethylammonium chloride, dicocoyldimethylammonium chloride, gluconamidopropyldimethylhydroxyethylammonium chloride, di[polyoxyethylene(2)]oleylmethylammonium chloride, dodecyldimethylethylammonium chloride, octyldihydroxyethylmethylammonium chloride, tri[polyoxyethylene(5)]-stearylammonium chloride, polyoxypropylenemethyldiethylammonium chloride, lauryldimethyl(ethylbenzyl)ammonium chloride, behenamidopropyl-N,N-dimethyl-N-(2,3-dihydroxypropyl)ammonium chloride, tallowdimethylammoniopropyltrimethylammonium dichloride, and benzalconium chloride.

A second group of suitable biocides include copper, zinc, silver, salts of chlorides, chlorites, perchlorates, hypochlorites, sulfates, sulfites, bisulfates, bisulfites, nitrates, nitrites and hydroxides. Also colloid metal such as silver, gold, copper and zinc have superior biocidal properties. Colloidal silver, gold, copper and zinc are extracted and created as ultrafine (0.010-0.001 micron) particles.

A third group of suitable biocides include organic acids which are safe under the FDA GRAS guidelines for food production yet still effective in controlling bacteria. The basic principle action of organic acids on bacteria is that non-dissociated organic acids can penetrate a bacterium cell wall and cause disruption due to the fact it cannot tolerate a wide internal and external pH gradient. This will cause the osmotic pressure inside the cell to increase which state is incompatible with bacterial survival.

A first group of suitable organic acids are Lactic acid, Acetic acid, Formic acid, Fumaric acid, Citric acid, Oxalic acid, Adipic acid and Uric acid.

A second group of suitable organic acids are the carboxylic acids, whose acidity is associated with their carboxyl group —COOH. Sulfonic acids, containing the group —SO$_2$OH, are relatively stronger acids. The relative stability of the conjugate base of the acid determines its acidity. In some biological systems more complex organic acids such as L-lactic, citric, and D-glucuronic acids are formed. These use the hydroxyl or carboxyl group.

A third group of suitable organic acids are Humic, Sebacic, Stearic, Gallic, Palmitic, Caffeic, Glyoxylic, Fulvic, Carnosic, Anthranilic, Ellagic, Lipoic, Chlorogenic, Rosmarinic, Phosphoric, Methacrylic, Oleanic, Nitrohumic, Florocinnamic, Hexaflorosilicic, Hydrofluoric, Hydroxycitric and Silicofluoric.

A fourth group of suitable organic acids is fruit acids. The acids in fruits are chiefly acetic, malic, citric, tartaric, oxalic, and in some instances boric. Malic acid is present in apples, pears, currants, blackberries, raspberries, quince, pineapple, cherries, and rhubarb. Citric acid is found in lemons, oranges, grapefruit, lemons, limes, quince, gooseberry, strawberry, raspberry, currant, and cranberry. Tartaric acid occurs in grapes. Boric acid is found in many fresh fruits and vegetables. Mandelic acid is present in almonds.

A fifth group of suitable organic acids is beta hydroxy acids, which is a type of phenolic acid. Salicylic acid is a colorless crystalline organic acid whose main active ingredient obtained from this source is a monohydroxiybenzoic acid.

A sixth group of suitable organic acids is a class of products that break biofilm. Biofilms are the protective layer/barrier that surround bacteria. Some species are not able to attach to a surface on their own but are often able to anchor themselves to the matrix or the bacteria cells. It is during this colonization that the cells are able to communicate via its quorum sensing ability. Once colonization has begun, the biofilm grows through a combination of cell division and recruitment. The final stage of biofilm formation is known as development and is the stage in which the biofilm is established and may only change in shape and size. The development of a biofilm may allow for an aggregate cell colony to be increasingly resistant. A biofilm's hard protective surface can be broken by *Lactobacillus sc Nisin* which is produced by fermentation using the bacterium *Lactococcus lactis*. This is obtained from the culturing of *Lactococcus lactis* on natural substrates, such as milk or dextrose, and is not chemically synthesized. This is a peptide which is produced by the food grade dairy starter bacterium *Lactococcus lactis*.

A seventh group of suitable organic acids is natural enzymes. Enzymes are proteins that catalyze chemical reactions and range from just 62 amino acid residues. Typically these are protease, lipase, diastase and cellulase enzymes. Enzymes are usually very specific as to which reactions they catalyze and the substrates that are involved in these reactions. The shape, charge and hydrophilic/hydrophobic nature characterize the enzymes.

pH Buffer

The pH buffer is a biocidal, dermal, non-corrosive acid composition, having a proton count range of from $1.0 \times 10^{20}$ to $9.9 \times 10^{26}$, an embodied conductivity range of from 250 mV to 1500 mV and a 0.1% solution of the composition having a pH of under 2.0.

Surfactant

The disclosed compositions comprise from about 0.05% to about 5.0% by weight of a cationic surfactant having an HLB of from about five to about 30. One aspect of the disclosed compositions comprises a cationic or ionic surfactant having an HLB of from about 12 to about 18. A further aspect of the disclosed compositions comprises a cationic or ionic surfactant having an HLB of from about 13 to about 16. Another embodiment of the disclosed compositions comprise from about 0.1% to about 4.0% by weight of a cationic or ionic surfactant.

Suitable cationic or ionic surfactants for use in the disclosed compositions include polyoxyethylene C6-C12 alkylphenyl ethers, polyoxyethylene sorbitan tri(C12-C18)-alkanoates, polyoxyethylene sorbitan di(C12-C18)-alkanoates, polyoxyethylene sorbitan mono-, di-, and tri-(C12-C18)-alkanoates, and polyoxyethylene C12-C20 alkyl ethers.

One category of suitable cationic or ionic surfactants for use in the disclosed compositions are the polyoxyethylene $C_6$-$C_{12}$ alkylphenyl ethers having the formula:

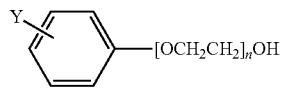

where Y is a $C_6$-$C_{12}$ alkyl unit and n is an index from 5 to 40. Non-limiting examples of $C_6$-$C_{12}$ alkylphenyl ethers includes polyoxyethylene(5) isooctylphenyl ethers sold under the tradenames IGEPAL™ CA-520 and IGEPAL™ CO-520, polyoxyethylene(8) isooctylphenyl ethers sold under the tradename TRITON™ X-114, polyoxyethylene(9) nonylphenyl ether sold under the tradename IGEPAL™ CO-630, polyoxyethylene(10) isooctylphenyl ether sold under the tradename TRITON™ X-100, polyoxyethylene (branched) nonylphenyl ethers sold under the tradename TRITON™ N-101, polyoxyethylene(12) nonylphenyl ether sold under the tradename IGEPAL™ CO-720, polyoxyethylene(12) isooctylphenyl ether sold under the tradename IGEPAL™ CA-720, polyoxyethylene(40) nonylphenyl ether sold under the tradename IGEPAL™ CO-890, and polyoxyethylene(40) isooctylphenyl ether sold under the tradename TRITON™ X-405.

Another category of cationic or ionic surfactants for use in the disclosed compositions are polyoxyethylene sorbitan mono-, di-, and tri-($C_{12}$-$C_{18}$)-alkanoates, non-limiting examples of which include polyoxyethylene(20) sorbitan trioleate sold under the tradename TWEEN™ 85, polyoxyethylene(20) sorbitan monooleate sold under the tradename TWEEN™ 80, polyoxy-ethylene(20) sorbitan monostearate sold under the tradename TWEEN™ 60, polyoxyethyl-ene (20) sorbitan monopalmitate sold under the tradename TWEEN™ 40, and polyoxyethyl-ene(20) sorbitan monolaurate sold under the tradename TWEEN™ 20.

A further category of cationic or ionic surfactants for use in the disclosed compositions are polyoxyethylene $C_9$-$C_{20}$ alkyl ethers, non-limiting examples of which include ethoxylate alcohols having the formula: RO(CH$_2$CH$_2$O)$_m$H, wherein R is a linear or branched alkyl group having from 6 to 20 carbon atoms and m is an integer of about 2 to about 20. On example of suitable ethoxylate alcohol surfactants are the NEODOL™ ethoxylated alcohols from Shell Chemicals. Non-limiting examples of suitable ethoxylated alcohols include NEODOL™ 91-5, NEODOL™ 91-6, NEODOL™ 91-8, NEODOL™ 91-9, NEODOL™ 23-6.5, NEODOL™

25-5, NEODOL™ 25-7, NEODOL™ 25-9, NEODOL™ 25-12, NEODOL™ 45-7, and NEODOL™ 135-7.

Carriers

The balance of the disclosed compositions comprises a carrier. The carrier can be any suitable material that can dissolve the active ingredients and co-ingredients and deliver the biocidal system to the infected areas. Water is a convenient carrier for liquid embodiments of the disclosed composition.

Adjunct Ingredients

The disclosed compositions can further comprise one or more dyes at levels of from about 0.001% to 0.5%. Non-limiting examples of suitable dyes are Alizarine Light Blue B (C.I. 63010), Carta Blue VP (C.I. 24401), Acid Green 2G (C.I. 42085), Astrogen Green D (C.I. 42040), Supranol Cyanine 7B (C.I. 42675, Maxilon Blue 3RL (C.I. Basic Blue 80), Drimarine Blue Z-RL (C.I. Reactive Blue 18), Alizarine Light Blue H-RL (C.I. Acid Blue 182), FD&C Blue No. 1 and FD&C Green No. 3. (See U.S. Pat. Nos. 4,248,827 and 4,200,606, both incorporated herein by reference.).

Other colors which can be Lakes that may be used are FD&C Blue No. 1-Brilliant Blue FCF, (blue shade), FD&C Blue No. 2-Indigotin, (dark blue shade), FD&C Green No. 3-Fast Green FCF, (turquoise shade), FD&C Red No. 40-Allura Red AC, (red shade), FD&C Red No. 3-Erythrosine, (pink shade, commonly used in glace cherries), FD&C Yellow No. 5-Tartrazine, (yellow shade), FD&C Yellow No. 6-Sunset Yellow FCF, E110 (orange shade)

Another adjunct ingredient suitable for use in the compositions disclosed herein includes fragrances.

Formulations

TABLE I

| Ingredients | Amount (wt %) |
| --- | --- |
| Malic Acid | 0.15-1.50 |
| pH buffer | 0.05-2.00 |
| Thickener | 0.50-4.00 |
| Carrier | balance |
| Adjunct Ingredients | trace |

TABLE II

| Ingredients | Amount (wt %) |
| --- | --- |
| Cetyl pyridinium chloride | 0.10-1.0 |
| pH buffer | 0.05-2.0 |
| PEG 6 | 0.35-5.0 |
| Thickener | 0.25-4.0 |
| Carrier | balance |
| Adjunct Ingredients | trace |

Table I represents an environmentally friendly composition formulated in accordance with embodiments of the invention comprising an organic acid in place of a quaternary ammonium salt.

Methods of Use

The disclosed compositions can be used in various applications. The application route and dosage regimen is dictated by the type and count of the microbial contaminant. As an example of possible applications of the invention, the compositions can be used on a variety of contaminated surfaces in order to reduce infection or contamination to humans and animals coming in contact with that surface. The compositions can be applied as a cleanser, scrub (cleanser with abrasive properties), spray, foam, fog, or gel.

An effective amount may vary according to factors known in the art, such as the type of microbial contaminant, the microbial count and the type of surface being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the contaminated surface. In addition, the compositions of the present disclosure can be administered as frequently as necessary to achieve desired results.

Working Examples

The following procedures were used to evaluate the disclosed compositions against various microbiologically contaminants. The composition tested in each of the below examples comprised 0.25 wt % malic acid, 0.10 wt % pH buffer, and 0.5 wt % thickener. The results below further indicate the effectiveness of the disclosed compositions.

Bacterial testing was done using *Staphylococcus aureus* ATCC #6538. The results are listed in Table A. The reduction in bacterial growth was a 99.9999%.

TABLE A

| Species | Control units | Results units |
| --- | --- | --- |
| *Staphylococcus aureus* | $7.9 \times 10^7$ cfu/ml | 2.5 cfu/ml |

Bacterial testing was completed at Biological Consulting Services of North Florida, Inc. on *E. coli* (ATCC 15597), *Salmonella enterica* (ATCC BAA-711), and Methicillin Resistant *Staphylococcus aureus* (MRSA; BAA-44). The results are listed in Table B.

TABLE B

| Sample | Control units (cfu/ml) | Results units (cfu/ml) |
| --- | --- | --- |
| *E. coli* | $9.3 \times 10^5$ | <0.5 |
| *S. enterica* | $1.1 \times 10^6$ | <0.5 |
| MRSA | $1.0 \times 10^6$ | <0.5 |

Viral tests were completed at Biological Consulting Services of North Florida, Inc. on the following on the following Orthomyxviridie virus ATCC type CCL-34, Influenza A/Equi 2 (ATCC VR517) *Poliovirus* 1 (Chat; ATCC VR-1562), and *Rhinovirus* 39 (ATCC VR-340). The results of the viral tests are shown in Table C.

TABLE C

| Sample | Control units | Results units |
| --- | --- | --- |
| Orthomyxviridie virus | $6.2 \times 10^6$ | <200 cfu/ml |
| Influenza A (H1N1) | $3.1 \times 10^4$ | <200 cfu/ml |
| Poliovirus 1 | $1.6 \times 10^5$ | $2.1 \times 10^{\wedge}1$ |
| Rhinovirus 39 | $6.7 \times 10^5$ | <200 cfu/ml |

Mold and fungi tests were completed at Biological Consulting Services of North Florida, Inc. on the following on the following *Trichophyton mentagrophytes* ATCC 4807, *Guignardia citricarpa* ATCC 26254, and *Colletotrichum acutatum* (ATCC 38689). The results of the mold and fungi tests are shown in Table D.

TABLE D

| Sample | Control units (cfu/ml) | Results units (cfu/ml) |
| --- | --- | --- |
| *Trichophyton mentagrophytes* | $1.1 \times 10^4$ | <1.0 |
| *Guignardia citricarpa* | $1.9 \times 10^4$ | <1.0 |
| *Colletotrichum acutatum* | $1.5 \times 10^4$ | <1.0 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A composition for preventing microbiological contamination or reducing a microbial count associated with a contaminated surface comprising:
   a. about 0.01% to about 20.0% by weight of a biocidal system comprising:
      i. from about 0.01% to 25% by weight of a primary biocide, wherein the primary biocide is citric acid; and
      ii. at least about 0.01% to 25% by weight of a pH buffer, where the pH buffer is a biocidal, dermal, non-corrosive acid composition, having a proton count range of $1.0 \times 10^{20}$ to $9.9 \times 10^{26}$, an embodied conductivity of 250 mV and has a pH of less than 2.0 when the pH buffer is present at a concentration of 0.1% by weight; and
   b. from about 0.01% to 2.0% by weight of a surfactant, wherein the surfactant is a combination of polyoxyethylene (20) sorbitan trioleate and ethoxylated partial glyceride fatty acid esters; and
   c. a balance of the composition being an aqueous based carrier.

2. The composition according to claim 1 further comprising a cationic or ionic surfactant with a hydrophile-lipophile balance of from about 12 to about 18.

3. The composition according to claim 1 further comprising a cationic or ionic surfactant with a hydrophile-lipophile balance of from about 13 to about 16.

4. A composition for preventing microbiological contamination or reducing a microbial count associated with a contaminated surface comprising:
   a. about 0.01% to about 20.0% by weight of a biocidal system comprising:
      i. from about 0.01% to 25% by weight of a primary biocide, wherein the primary biocide is citric acid; and
      ii. at least about 0.01% to 25% by weight of a pH buffer, where the pH buffer is a biocidal, dermal, non-corrosive acid composition, having a proton count of $1.0 \times 10^{20}$, an embodied conductivity range of 250 mV to 1500 mV and has a pH of less than 2.0 when the pH buffer is present at a concentration of 0.1% by weight; and
   b. from about 0.01% to 2.0% by weight of a surfactant, wherein the surfactant is a combination of polyoxyethylene (20) sorbitan trioleate and ethoxylated partial glyceride fatty acid esters; and
   c. a balance of the composition being an aqueous based carrier.

5. A composition for preventing microbiological contamination or reducing a microbial count associated with a contaminated surface comprising:
   a. about 0.01% to about 20.0% by weight of a biocidal system comprising:
      i. from about 0.01% to 25% by weight of a primary biocide, wherein the primary biocide is citric acid; and
      ii. at least about 0.01% to 25% by weight of a pH buffer, where the pH buffer is a biocidal, dermal, non-corrosive acid composition, having a proton count of $1.0 \times 10^{20}$, an embodied conductivity of 250 mV and has a pH of less than 2.0 when the pH buffer is present at a concentration of 0.1% by weight; and
   b. from about 0.01% to 2.0% by weight of a surfactant, wherein the surfactant is a combination of polyoxyethylene (20) sorbitan trioleate and ethoxylated partial glyceride fatty acid esters; and
   c. a balance of the composition being an aqueous based carrier.

* * * * *